United States Patent [19]

Fischer

[11] Patent Number: 5,532,386

[45] Date of Patent: Jul. 2, 1996

[54] CATALYTIC PROCESS FOR ELIMINATING CARBOXYLIC ESTER AND ACYL GROUPS FROM ORGANIC COMPOUNDS

[75] Inventor: Rolf Fischer, Heidelberg, Germany

[73] Assignee: BASF Aktiengesellschaft, Ludwigshafen, Germany

[21] Appl. No.: 396,606

[22] Filed: Mar. 1, 1995

[30] Foreign Application Priority Data

Mar. 7, 1994 [DE] Germany .......................... 44 07 494.8

[51] Int. Cl.$^6$ ................................................ C07D 307/32
[52] U.S. Cl. ........................ 549/322; 549/425; 558/435; 560/120
[58] Field of Search .................................... 549/322, 425; 560/120; 558/435

[56] References Cited

U.S. PATENT DOCUMENTS

| | | | |
|---|---|---|---|
| 3,299,100 | 1/1967 | Phillips | 260/343.6 |
| 4,276,225 | 6/1981 | Lantzsch et al. | 260/408 |
| 4,417,073 | 11/1983 | Ackermann et al. | 560/105 |
| 4,422,979 | 12/1983 | Zaiko et al. | |

FOREIGN PATENT DOCUMENTS

| | | |
|---|---|---|
| 546395 | 6/1993 | European Pat. Off. . |
| 602515 | 6/1994 | European Pat. Off. . |
| 62-201843 | 9/1987 | Japan . |

OTHER PUBLICATIONS

Chem. Abst. vol. 109, 14925 (1988).
Tetrahedron Lts. vol. 27, No. 15, p. 1639, (1986).
Q. Rev. Chem Sec. 7, 175 (1953).
Chem. Rev. 57, 191 (1957).
Arch. Pharm. 319, 25 (1986).

*Primary Examiner*—Jacqueline Haley
*Attorney, Agent, or Firm*—Keil & Weinkauf

[57] ABSTRACT

A process for preparing compounds of the formula I

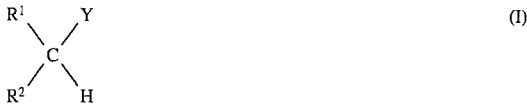

where:
Y inter alia is

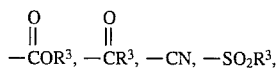
$-COR^3, -CR^3, -CN, -SO_2R^3,$ where $R^3$ is hydrogen or a $C_1-C_{10}$- hydrocarbon radical. $R^1$ and $R^2$, inter alia, are each, independently of one another, hydrogen, a $C_1-C_{20}$-hydrocarbon radical which optionally carries inert substituents or heteroaryl, wherein a compound of the formula II

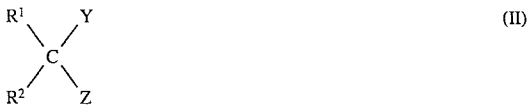

where Z is

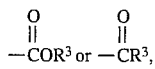
$-COR^3$ or $-CR^3,$ is reacted in the presence of catalytic amounts of a carbonic ester and of a nitrogenous base at from 100° to 250° C. under a pressure of from 0.01 to 100 bar.

11 Claims, No Drawings

CATALYTIC PROCESS FOR ELIMINATING CARBOXYLIC ESTER AND ACYL GROUPS FROM ORGANIC COMPOUNDS

The present invention relates to a process for preparing compounds of the formula I

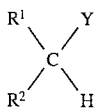

where:
Y is

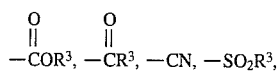

where $R^3$ is hydrogen or a $C_1$–$C_{10}$ hydrocarbon radical, phenyl, which carries inert substituents if desired, or together with $R^1$ is

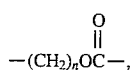

where n is an integer from 2 to 4, $R^1$ and $R^2$ are each, independently of one another, hydrogen, a $C_1$–$C_{20}$ hydrocarbon radical which carries inert substituents if desired, or heteroaryl, furthermore $C_1$–$C_6$-acyl, when Y is

or together are a $C_1$–$C_{12}$-alkylene bridge which may contain as bridge member oxygen, sulfur or $NR^4$ where $R^4$ is hydrogen or $C_1$–$C_4$-alkyl, which process comprises reacting a compound of the formula II

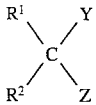

where Z is

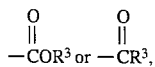

in the presence of catalytic amounts of a carbonic ester and of a nitrogenous base.

Geminal dicarboxylic diesters can be converted in three reaction stages by alkaline hydrolysis to the corresponding geminal dicarboxlic acid, subsequently by thermal elimination of a carboxyl group and esterification of the remaining carboxyl group into monocarboxylic esters (JP-A-62/201 843; Chem. Abstr. Vol. 109, 14925).

It is furthermore known that heating of geminal dicarboxylic diesters with mixtures of mineral acids and carboxylic acids results in corresponding monocarboxylic acids (Arch. Pharm. 319 (1986) 29) which subsequently have to be esterified to the desired monocarboxylic esters.

Tetrahedron Lett. 27 (1986) 2283 discloses a one-stage conversion of geminal dicarboxylic diesters into monocarboxylic esters by heating in polar solvents such as dimethyl sulfoxide or dimethylformamide in the presence of alkali metal chlorides or cyanides.

Finally, geminal dicarboxylic diesters can, as disclosed in EP-A 546 395, be converted in one stage into monocarboxylic esters on oxide catalysts, preferably in the gas phase at 250°–350° C.

The first two methods for preparing carboxylic esters from geminal dicarboxylic esters have the disadvantage that several reaction stages are necessary and that in the first case salt is produced. Very long reaction times are necessary for the third, one-stage synthesis. The fourth method, which is carried out at high temperatures, is conditional on the vaporizability and the thermal stability of the starting compounds so that it cannot be used for all desired reaction products.

Acyl groups in compounds derived from acetoacetic esters can be eliminated by heating with alcoholic alkanolate solutions (F. D. Gunstone, Q. Rev. Chem. Soc. 7 (1953) 175 and W. J. Gensler, Chem. Rev. 57 (1957) 191).

In a similar way, according to U.S. Pat. No. 4,422,979, ester groups can be eliminated from cyanoacetic esters substituted by alkyl and phenyl radicals.

Since the alkanolates must be hydrolyzed when working up the reaction mixtures, these two methods are associated with production of salt.

It is an object of the present invention to provide a process which avoids the abovementioned disadvantages in the elimination of acyl and carboxylic ester groups from organic compounds.

We have found that this object is achieved by the process, defined at the outset, for preparing compounds of the formula I, which comprises reacting a compound of the formula II

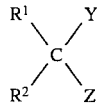

where Z is

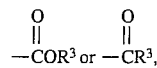

in the presence of catalytic amounts of a carbonic ester and of a nitrogenous base.

The advantage compared with the use of alcoholates in alcohols as solvents is that the materials used according to the invention carbonic diesters and nitrogenous bases—are not, like alcoholates, easily hydrolyzed and that rigorous exclusion of moisture is therefore unnecessary. Workup with water does not lead, as in the case of the alcoholates, to waste waters containing mineral salts.

The process according to the invention can be represented in the case of the elimination of an ester group from a geminal dicarboxylic diester such as dimethyl dimethylmalonate using dimethyl carbonate, ethyldimethylamine and methanol by the equation

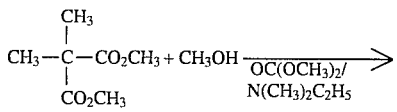

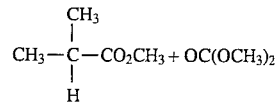

and in the case of the elimination of an acetyl group from a compound derived from acetoacetic ester, such as 2-acetylbutyrolactone, using dimethyl carbonate, ethyldimethylamine and methanol by the equation

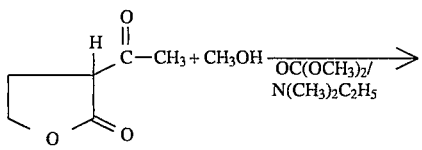

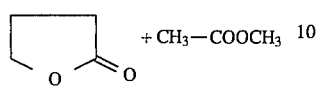

The radicals in the products I and in the starting compounds II are defined above. Specifically these are:

is a radical derived from a carboxylic acid or carboxylic ester, such as methoxycarbonyl, ethoxycarbonyl, also formyl, acyl such as acetyl, propanoyl, moreover cyano, a radical derived from a sulfonic ester or an alkylsulfonyl radical such as methylsulfonyl, or is phenyl which can carry from one to three inert substituents, for example halogen such as fluorine, chlorine, bromine and iodine, $C_1$–$C_6$-alkoxy such as methoxy and ethoxy, cyano, nitro, and in conjunction with $R^1$ is an alkyl ester bridge.

is preferably a carboxylic ester group and Y is a carboxylic ester, cyano or acyl group.

$R^1$ and $R^2$ are, apart from hydrogen, also $C_1$–$C_{20}$ hydrocarbon radicals such as straight-chain or branched alkyl groups with, preferably, 1 to 6 carbon atoms, e.g. methyl, ethyl, n-propyl, isopropyl, n-butyl, sec-butyl. These groups may carry inert substituents such as halogen atoms. However, carboxylic ester groups are also suitable as such inert substituents, as in methoxycarbonylmethyl.

Also suitable are cycloalkyl groups with, preferably, 3 to 8 carbon atoms such as cyclopropyl, cyclobutyl, cyclopentyl, cyclohexyl.

Other hydrocarbon radicals which should be mentioned are biphenyl and aryl radicals such as phenyl.

Also suitable are aralkyl radicals such as benzyl, which may likewise be substituted in the aromatic ring as described above for Y. Heteroaryl radicals which should be mentioned are thienyl and pyridyl.

Furthermore, $R^1$ and $R^2$ may together form a $C_1$–$C_{12}$-alkylene bridge such as in sulfolane, which may contain heteroatoms so that an example of a compound I is a butyrolactone derivative.

When Y is a group derived from a carboxylic acid or carboxylic ester, $R^1$ and $R^2$ can be $C_2$–$C_6$-acyl, e.g. acetyl as in dimethyl 2-acetyl malonate.

The $R^3$ radicals in the substituents Y and Z can be identical or different.

Examples of preferred starting compounds of the formula II are malonic diesters substituted in position 2, such as dimethyl 2-methylmalonate, diethyl 2-methylmalonate, dimethyl 2-acetylmalonate, diethyl 2-phenylmalonate, dimethyl 2,2-dimethylmalonate, dipropyl 2,2-diacetylmalonate, dimethyl 2-benzylmalonate, also dimethyl 1,1-cyclopropanedicarboxylate, diethyl 1,1-cyclohexanedicarboxylate, dimethyl tetrahydropyran-4,4-dicarboxylate, dimethyl tetrahydrothiopyran-4,4-dicarboxylate, dimethyl 1,1-cyclopentanedicarboxylate, methyl 2,2-dimethylcyanoacetate, methyl 2-methyl-2-n-butylcyanoacetate, dimethyl 2-formylsuccinate, methyl 2,2-dimethylacetate, 3-methyl-3-butylacetylacetone, ethyl 2-methyl-2-(o-methoxyphenyl) cyanoacetate, ethyl 2-methyl-2-(o-fluorobiphenylyl) cyanoacetate, ethyl 2-thienylcyanoacetate, ethyl 2-methyl-2-(m-ethoxyethylphenyl) cyanovalerate, dimethyl 2-methyl-2-(m-chloro-p-methoxyphenyl) malonate, 2-acetylbutyrolactone, 2-methyl-2-acetylbutyrolactone, 2-methoxycarbonylbutyrolactone, 2-methyl-2-carbomethoxysulfolane, 2-carbomethoxy sulfolane.

The compounds II required for the reaction according to the invention are commercially available or can be prepared by conventional methods, e.g. by mono- or dialkylation or acylation of malonic diesters, cyanoacetic esters, acetoacetic esters and phenylacetonitriles.

The process according to the invention can be carried out as follows: lows:

The compounds of the formula II can be reacted in the presence of nitrogenous bases at from 100° to 250° C., preferably 130 to 230° C., particularly preferably 150° to 210° C. and under from 0.01 to 100 bar, preferably 5 to 50 bar, particularly preferably under the pressure set up in the reaction mixture.

The reaction can be carried out in the liquid phase batchwise or continuously, for example in an autoclave.

In the preparation of products which are sensitive to hydrolysis, it may be advantageous to carry out the reaction in the presence of gases which are inert under the reaction conditions, such as nitrogen or argon.

Compounds I can be prepared in the liquid phase for example by heating a compound II in the presence of carbonic diesters and a nitrogenous base to the required temperature. After the reaction is complete, the mixture can be cooled and fractionally distilled to obtain the desired compounds I.

The reaction according to the invention can be carried out in the absence of solvents. However, it may be advantageous for solvents to be present. Examples of solvents which can be used are acyclic or cyclic ethers such as diethyl ether, tetrahydrofuran and dioxane, aromatic hydrocarbons such as benzene, toluene and xylene, chlorinated hydrocarbons such as chloroform and methylene chloride.

The amount of solvent is from 0 to 90%, preferably 0 to 30%, of the weight of the compounds II.

Suitable carbonic diesters are dialkyl esters such as dimethyl, diethyl, diisopropyl, di-n-butyl and diallyl carbonates, diaryl esters such as diphenyl and ditolyl carbonates, cyclic esters such as ethylene and propylene carbonates, dibenzyl carbonate, cycloalkyl esters such as dicyclohexyl carbonate and mixed esters with aliphatic and aromatic radicals such as phenyl allyl and ethyl phenyl carbonates, as described, for example, in Kirk-Othmer, Encyclopedia of Chemical Technology, Fourth edition, Volume 5, (1993) pages 87–88.

Examples of suitable nitrogenous bases are ammonia or amines with 1 to 30 carbon atoms such as primary, secondary or tertiary amines with aliphatic, cycloaliphatic, heteroaromatic and/or araliphatic substituents. It is moreover possible for two substituents to form a ring. Also suitable are amines carrying functional groups such as hydroxyl groups, and aromatic amines and polyamines.

Examples thereof are:

ammonia, methylamine, ethylamine, hexylamine and cyclohexylamine, dimethylamine, diethylamine, dibutylamine and dicyclohexylamine, trimethylamine, dimethylethylamine, triethylamine, tri-n-propylamine, triisopropylamine, tributylamine, trioctylamine, tricyclohexylamine, trihexyldecylamine, tricyclohexylamine, diphenylmethylamine, dimethylbenzylamine, dibenzylmetyhylamine, tribenzylamine, N,N-tetrammethylhexammethylenediamine, hexamethylenediamine, tetramethylenediamine, ethanolamine, diethanolamine, triethanolamine, 4-dimethylaminopyridine, urotropine, piperidine, N-methylpiperdine pyrrolidine, N-methylpyrrolidine, hexamethyleneimine, N-ethylhexamethyleneimine, N-methylimidazole, 1,4-diazabicyclo[2.2.2]octane (DABCO), morpholine, piperazine, pyrrolidine, 2,6-dimethylmorpholine.

Also suitable are amidines such as 1,5-diazabicyclo[4.3.0]non-5-ene (DBN), 1,8-diazabicyclo[5.4.0]undec-7-ene (DBU) and guanidine.

Tertiary amines are preferred, particularly preferably $C_3$–$C_{24}$-trialkylamines. Also preferred are amidines such as DBN and DBU.

The molar ratio of the compounds II to the carbonic diesters and the nitrogenous bases is, as a rule, from 1:0.01:0.01 to 1:0.5:0.5, preferably 1:0.05:0.05 to 1:0.2:0.2. In general, the carbonic diesters and the nitrogenous bases are added to the reaction mixture;in approximately the equimolar ratio.

It has proven advantageous to carry out the process according to the invention in the presence of an alcohol.

Examples of alcohols which can be used are aliphatic, cycloaliphatic and araliphatic monohydric or polyhydric alcohols and phenols such as methanol, ethanol, n-propanol, i-propanol, butanols, decanols, dodecanols, ethylene glycol, 1,4-butanediol, 1,3-propanediol, glycerol, 1,8-octanediol, cyclohexanol, cyclopentanol, 1,4-cyclohexanediol, benzyl alcohol and phenol; $C_1$–$C_6$-alkanols are preferred. In order to obtain pure monoesters from the elimination of ester groups from geminal dicarboxylic esters it may be worthwhile to use those alcohols present in the ester groups.

The molar ratio of the compounds II to the alcohols is, as a rule:, from 1:0.1 to 1:5, in particular 1:0.5 to 1:1.5.

As a rule, the reactions take from 0.1 to 10 hours.

The products are used, for example, as precursors for pharmaceuticals and crop protection agents.

were heated to 200° C. in a stirred autoclave and kept at this temperature for three hours. The molar ratios of the reactants are listed in Table 1. After the autoclave had been cooled and decompressed, the reaction mixture was weighed. The products were identified by coupled GC-MS and comparison of the GC retention times with reference substances. The yields of compounds I in Table 1 were determined by quantitative GC analysis.

The by-product of the elimination of a methoxycarbonyl group was dimethyl carbonate, and that in the case of an acetyl group was methyl acetate. These compounds were isolated in yields of from 44 to 74%.

The following products were prepared:

Example 1

Methyl 2-methylpropionate from dimethyl dimethylmalonate

Example 2

Methyl cyclohexanecarboxylate from dimethyl cyclohexane-1,1-dicarboxylate

Example 3

Methyl propionate from dimethyl methylmalonate

Example 4

Methyl tetrahydropyran-4-carboxylate from dimethyl tetrahydropyran-4,4-dicarboxylate

Example 5

2-Methylhexanonitrile from methyl 2-methyl-2-butylcyanoacetate

Example 6

Butyrolactone from 2-acetylbutyrolactone

Example 7

2-Methylbutyrolactone from 2-acetyl-2-methylbutyrolactone

TABLE 1

| | | | | | | | | |
|---|---|---|---|---|---|---|---|---|
| Example | Starting compound II | | | | Molar ratio | Product I [%] | | |
| No. | $R^1$ | $R^2$ | Y | Z | II:1:2:3 | Y | C | S |
| 1 | —CH₃ | —CH₃ | | | 1:0.2:0.2:1 | 86 | 94 | 91 |
| 2 | —CH₂—(CH₂)₃—CH₂— | | | | | 75 | 90 | 83 |
| 3 | —CH₃ | H | —CO₂CH₃ | | | 51 | 100 | — |
| 4a | —(CH₂)₂—O—(CH₂)₂— | | | —CO₂CH₃ | 1:0.1:0.1:1 | 91 | 100 | — |
| 4b | | | | | 1:0.05:0.05:1 | 93 | 99 | 94 |
| 5 | —CH₃ | C₄H₉ | —CN | | 1:0.2:0.2:1 | 93 | 100 | — |
| 6 | R¹/Y: —(CH₂)₂—O—C(=O)— | R²: H | | —CO—CH₃ | | 50 | 100 | |
| 7 | | —CH₃ | | | | 69 | 100 | |

Y Yield
C Conversion
S Selectivity

EXAMPLES

General preparation method for Examples 1–7

Mixtures of the starting compounds II (0.05 mol), ethyldimethylamine 1, dimethyl carbonate 2 and methanol 3

Example 8

Example 1 was repeated but with the difference that ethyldimethylamine was replaced with the same molar quantity of triethylamine. Quantitative analysis by gas chromatography showed an 88% yield of methyl isobutyrate with a conversion of 96%.

Example 9

Example 1 was repeated but with the difference that ethyldimethylamine was replaced by the same molar quantity of 1,8-diazabicyclo[5.4.0]undec-7-ene (DBU). Quantitative analysis by gas chromatography showed a 94% yield of methyl isobutyrate with quantitative conversion.

Example 10

Example 1 was repeated but with the difference that dimethyl carbonate was replaced by the same molar quantity of diethyl carbonate and methanol was replaced by the same molar quantity of ethanol. Quantitative analysis by gas chromatography showed a 44% yield of methyl isobutyrate and a 33% yield of ethyl isobutyrate with a conversion of 85%.

Example 11

Example 1 was repeated but with the difference that dimethyl carbonate was replaced by the same molar quantity of diphenyl carbonate. Quantitative analysis by gas chromatography showed a 90% yield of methyl isobutyrate with a conversion of 95%.

Example 12 (without alcohol)

A mixture of 6.8 g of methyl 2-(n-butyl)-2-methylcyanovalerate, 0.18; g of dimethyl carbonate, 0.15 g of ethyldimethylamine and 1.6 g of tetrahydrofuran was heated at 200° C. for 3 hours. Quantitative analysis by gas chromatography showed a 22% yield of 2-methylcapronitrile with a conversion of 53%.

I claim:

1. A process for preparing compounds of the formula I

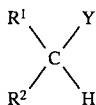   (I)

where:
Y is

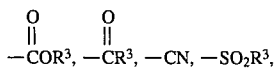

where $R^3$ is hydrogen or a $C_1$–$C_{10}$ hydrocarbon radical, phenyl, which carries inert substituents if desired, or together with $R^1$ is

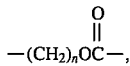

whereon n is an integer from 2 to 4, $R^1$ and $R^2$ are each, independently of one another, hydrogen, a $C_1$–$C_{20}$ hydrocarbon radical which carries inert substituents if desired, or heteroaryl, furthermore $C_1$–$C_6$-acyl, when Y is

or together are a $C_1$–$C_{12}$-alkylene bridge which may contain as bridge member oxygen, sulfur or $NR^4$ where $R^4$ is hydrogen or $C_1$–$C_4$-alkyl, which process comprises reacting a compound of the formula II

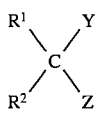   (II)

where Z is

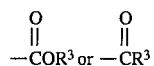

in the presence of catalytic amounts of a carbonic ester and of a nitrogenous base.

2. The process of claim 1, wherein dimethyl carbonate is used as carbonic ester.

3. A process as claimed in claim 1, wherein $C_3$–$C_{24}$-trialkylamines, 1, 5-diazabicyclo[4.3.0]non-5-ene (DBN) or 1,8-diazabicyclo[5.4.0]undec-7-ene (DBU) is used as nitrogenous base.

4. A process as claimed in claim 2, wherein $C_3$–$C_{24}$-trialkylamines, 1, 5-diazabicyclo[4.3.0]non-5-ene (DBN) or 1, 8-diazabicyclo[5.4.0]undec-7-ene (DBU) is used as nitrogenous base.

5. A process as claimed in claim 1, wherein the molar ratio of the compound II to the carbonic ester and to the nitrogenous base is from 1:0.05:0.05 to 1:0.2:0.2.

6. A process as claimed in claim 2, wherein the molar ratio of the compound II to the carbonic ester and to the nitrogenous base is from 1:0.05:0.05 to 1:0.2:0.2.

7. A process as claimed in claim 3, wherein the molar ratio of the compound II to the carbonic ester and to the nitrogenous base is from 1:0.05:0.05 to 1:0.2 :0.2.

8. A process as claimed in claim 1, wherein the reaction is carried out at from 100° to 250° C.

9. A process as claimed in claim 1, wherein the reaction is carried out in the presence of a $C_1$–$C_6$-alkanol.

10. A process as claimed in claim 2, wherein the reaction is carried out in the presence of a $C_1$–$C_6$-alkanol.

11. A process as claimed in claim 3, wherein the reaction is carried out in the presence of a $C_1$–$C_6$-alkanol.

* * * * *

UNITED STATES PATENT AND TRADEMARK OFFICE
CERTIFICATE OF CORRECTION

PATENT NO.: 5,532,386

DATED: July 2, 1996

INVENTOR(S): Rolf FISCHER

It is certified that error appears in the above-identified patent and that said Letters Patent is hereby corrected as shown below:

On the cover page, item [30], "44 07 494.8" should read --P 44 07 494.8--.

In the abstract, item [57] on the cover page, last line, "C." should be --C--.

Column 7, claim 1, line 57, "whereon" should be --where--.

Signed and Sealed this

Tenth Day of September, 1996

Attest:

BRUCE LEHMAN

Attesting Officer     *Commissioner of Patents and Trademarks*